United States Patent
Lee

(10) Patent No.: US 11,129,788 B1
(45) Date of Patent: Sep. 28, 2021

(54) SPRAYABLE FILM FORMING COMPOSITIONS FOR IMPROVING THE PERFORMANCE OF TOPICAL PREPARATIONS

(71) Applicant: ELC Management LLC, Melville, NY (US)

(72) Inventor: Wilson A. Lee, Hauppauge, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 16/827,876

(22) Filed: Mar. 24, 2020

(51) Int. Cl.
| | |
|---|---|
| *A61K 8/9706* | (2017.01) |
| *A61K 8/9794* | (2017.01) |
| *A61K 8/73* | (2006.01) |
| *A61K 8/81* | (2006.01) |
| *A61Q 19/00* | (2006.01) |
| *A61K 8/99* | (2017.01) |
| *A61K 8/49* | (2006.01) |
| *A61K 8/368* | (2006.01) |
| *A61K 8/9789* | (2017.01) |

(52) U.S. Cl.
CPC ............ *A61K 8/9706* (2017.08); *A61K 8/368* (2013.01); *A61K 8/498* (2013.01); *A61K 8/4953* (2013.01); *A61K 8/4973* (2013.01); *A61K 8/73* (2013.01); *A61K 8/735* (2013.01); *A61K 8/8147* (2013.01); *A61K 8/9789* (2017.08); *A61K 8/9794* (2017.08); *A61K 8/99* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2,949,403 | A | 8/1960 | Andreadis et al. |
| 4,708,865 | A | 11/1987 | Turner |
| 4,803,195 | A | 2/1989 | Holzner |
| 5,374,614 | A | 12/1994 | Behan et al. |
| 5,874,072 | A | 2/1999 | Alwattari et al. |
| 6,171,605 | B1 | 1/2001 | Bevacqua et al. |
| 6,403,109 | B1 | 6/2002 | Stora |
| 6,774,101 | B2 | 8/2004 | Stora et al. |
| 7,223,382 | B2 | 5/2007 | Sokolinsky et al. |
| 7,226,901 | B2 | 6/2007 | Stora |
| 7,323,162 | B2 | 1/2008 | Martin et al. |
| 7,655,613 | B2 | 2/2010 | Vlad et al. |
| 7,682,621 | B2 | 3/2010 | Lamberty et al. |
| 7,794,694 | B2 | 9/2010 | Giacomoni et al. |
| 7,846,889 | B2 | 12/2010 | Vlad et al. |
| 8,343,521 | B2 | 1/2013 | Shick et al. |
| 8,920,787 | B2 | 12/2014 | Li et al. |
| 8,932,570 | B2 | 1/2015 | Mu et al. |
| 9,072,686 | B2 | 7/2015 | Bui et al. |
| 9,078,835 | B2 | 7/2015 | Bui et al. |
| 9,301,910 | B2 | 4/2016 | Yontz |
| 2003/0186836 | A1 | 10/2003 | Dumanois et al. |
| 2004/0209795 | A1 | 10/2004 | Vlad |
| 2005/0053567 | A1 | 3/2005 | Liu |
| 2013/0202546 | A1* | 8/2013 | Howell |
| 2015/0004115 | A1 | 1/2015 | Tan et al. |
| 2018/0369119 | A1* | 12/2018 | Lee |

FOREIGN PATENT DOCUMENTS

| | | | | |
|---|---|---|---|---|
| FR | 2954155 | B1 | 2/2012 | |
| FR | 2954152 | B1 | 12/2012 | |
| JP | 2018177798 | A | * 11/2018 | ............... A61Q 1/02 |
| WO | WO-2016142092 | A1 | * 9/2016 | ............... A61Q 5/06 |

OTHER PUBLICATIONS

Becker et al., Final Report of the Safety Assessment of Hyaluronic Acid, Potassium Hyaluronate, and Sodium Hyaluronate, IJT 2009. (Year: 2009).*
Translated doc WO2016142092A1 (Year: 2016).*
Translated Doc JP2018177798A (Year: 2018).*
PCT International Search Report; International Application No. PCT/US2021/023533; Completion Date: Jul. 14, 2021; dated Jul. 14, 2021.
PCT Written Opinion of the International Searching Authority; International Application No. PCT/US2021/023533; Completion Date: Jul. 14, 2021; dated Jul. 14, 2021.

* cited by examiner

*Primary Examiner* — Susan Hoffman
*Assistant Examiner* — Jacob A Boeckelman
(74) *Attorney, Agent, or Firm* — Peter Giancana

(57) ABSTRACT

A spray-on film forming composition is designed to work with another topical preparation, such as a conventional cosmetic foundation or skincare product. The film forming composition is in direct contact with the cosmetic or skincare product. The spray-on film forming composition may be applied underneath a topical preparation (as a primer), on top of a topical preparation (as a mask), or both, depending on the benefit conferred. The spray-on film forming compositions of the invention are able to improve wearability and removability, increase shine, and deliver active ingredients. They are very clear, flexible and comfortable.

13 Claims, No Drawings

SPRAYABLE FILM FORMING COMPOSITIONS FOR IMPROVING THE PERFORMANCE OF TOPICAL PREPARATIONS

FIELD OF THE INVENTION

The present invention is in the field of topical preparations for keratinic surfaces. More specifically, the invention pertains to spray-on film forming compositions that improve the performance of underlying or overlying color cosmetic and skincare preparations.

BACKGROUND

Long wear cosmetic products are designed to resist smudging and transfer. But the ability to resist smudging and transfer also means that the product may be difficult to remove, when desired. A makeup remover product is often required, but even then it is a challenge to fully clean the skin. The face, for example, may be left with at least some residual product trapped in the pores. Also, makeup removers may have chemicals that are harsh to the skin, hair or nails. There is, therefore, a need for a way to make it easier to remove long wear cosmetic compositions when such is desired, while still resisting smudging and transfer, without resorting to harsh chemicals.

In co-pending application, US2018-0369119, we disclosed specific combinations of acrylates/VA copolymer (20-30% by weight of total composition) and acrylates copolymer (0.5-2.5% by weight of total composition) in an cosmetically acceptable aqueous base (40% to 65% of water by weight of total composition). Such compositions were useful as high shine color cosmetic compositions that are flexible and resistant to water below a certain minimum temperature (i.e. about 43° C.). The compositions wear well, are smudge and flake resistant, as well as oil resistant, making them very suitable as high shine, long wear cosmetics. However, unlike the compositions of the present invention, those compositions are not suitable as spray-on compositions that adhere to an adjacent cosmetic or skincare preparation. Compared to US2018-0369119, compositions of the present invention use different concentrations of acrylates/VA copolymer, acrylates copolymer and water, as well as other differences that confer benefits not found in the compositions of US2018-0369119.

SUMMARY

The present invention is a spray-on film forming composition. The spray-on film forming composition is designed to work with another topical preparation, such as a conventional cosmetic foundation or skincare product. The film forming composition is in direct contact with (that is, immediately "adjacent to") the cosmetic or skincare product. The spray-on film forming composition may be applied underneath a topical preparation (as a primer), on top of a topical preparation (as a mask), or both, depending on the benefit conferred. The spray-on film forming compositions of the invention are able to improve wearability (smudge and flake resistance, as well as oil resistance), improve removability, increase shine, and deliver active ingredients. They are very clear (invisible, if no colorant is used), flexible and comfortable, without a tacky feel.

Spray-on film forming compositions according to the invention comprise specific combinations of acrylates/VA copolymer and acrylates copolymer in a cosmetically acceptable base or delivery vehicle, with additional modifications not disclosed in US2018-0369119. The spray-on film and any adjacent cosmetic or skincare preparation are easily removed with light scrubbing by using water above a certain minimum temperature, but not as easily removed with water below that temperature.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are presented as percentages by weight of the final composition, unless otherwise specified.

Throughout the present specification, "film former" or the like refers to a polymer leaves a film on the substrate to which it is applied, for example, after a solvent accompanying the film former has evaporated, absorbed into and/or dissipated on the substrate. Spray-on film forming compositions according to the present invention typically dry within three minutes, preferably within two minutes, more preferably within one minute.

The term 'spray' or 'sprayable' means that a formulation is either dispensed by the use of propellant gas through a release valve to generate a mist of liquid (i.e. a conventional aerosol dispenser), or by a spray bottle with a mechanical pump dispenser that forces a liquid through a nozzle to generate a mist of liquid.

A "transfer resistant" composition of the invention is one that when applied to the skin or hair (either directly or on top of another preparation) for its intended use, is not readily removed by contact with another material, such as clothing or water. Transfer resistance may be evaluated by any method known in the art. In preferred embodiments of the present invention, little or no spray-on film forming composition, and little or no adjacent cosmetic or skincare composition, is transferred from the skin, lips, hair or nails to another substrate.

A "flexible" composition is one that when applied to the skin or hair (either directly or on top of another preparation) for its intended use, does not crack or flake for a defined period of time, such as four hours or eight hours of wear. If a composition is not adequately flexible, then it is "rigid".

By "single phase" it is intended that a composition is in a stable homogeneous form rather than in the form of a heterogeneous water-in-oil or oil-in-water emulsion. Some preferred embodiments of the present invention are aqueous single phase, and some are lightly emulsified oil-in-water emulsions.

"Comprising" and the like, mean that a list of elements may not be limited to those explicitly recited.

Acrylates/VA Copolymer

A first main ingredient of the invention is acrylates/VA copolymer (INCI name), $C_{15}H_{26}O_4$, also known as ethenyl acetate or 2-ethylhexyl prop-2-enoate (IUPAC names);

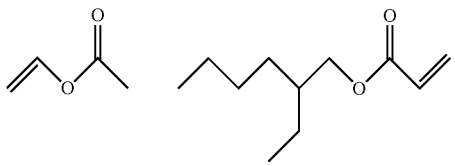

CAS number 25067-02-1. For detailed information, see PubChem Compound Database; CID=168269.

In cosmetics, this tacky material often functions as a binder, film former, adhesive and/or hair fixative. When deployed in aqueous cosmetic systems acrylates/VA copolymer can impart a film on the skin or hair. The pure acrylates/VA copolymer film features a temperature dependence, such that a water rinse of about 38° C. or more will degrade the film, and allow it to be removed from a surface, while retaining its integrity at temperatures at or below normal skin temperature (i.e. 36.5-37.5° C.).

Spry-on film forming compositions of the invention typically comprise about 4.7% to 14% of acrylates/VA copolymer by total weight of the composition, for example 7.0% to 12%, preferably about 9.3% by total weight of the composition. Concentrations of acrylates/VA copolymer a little below 4.7% may result in product transfer.

Acrylates/VA copolymer is commercially available, for example, as Vinysol 2140L from Daido Chemical Corp. Vinysol 2140L is a 46.6% aqueous mixture of acrylates/VA copolymer. Therefore, when using Vinysol 2140L, in order to achieve the concentrations of acrylates/VA copolymer noted above, the concentration of Vinysol 2140L should be about 10% to 30%, for example 15%-25.75%, preferably about 20% by total weight of the composition. Vinysol 2140L is reported to have a pH of 4.5, a viscosity of 2,000 mPa-s, a calculated glass transition temperature ($T_g$) of −9° C., while the film exhibits a break elongation of 1,200%, and a break strength of 1.2 MPa (when spread to a thickness 0.1 mm). By itself, the acrylates/VA copolymer is somewhat too rigid for consumer acceptance.

Acrylates Copolymer

To address the problem of high rigidity, the acrylates/VA copolymer was combined with an acrylates polymer that has a lower $T_g$ than acrylates/VA copolymer. In general, a lower $T_g$ provides more flexibility to the resulting film. It also increases the dry time of the film to a useful degree. Of course, a spray-on film forming composition that dries too fast or too slow is not commercially viable. In the present invention, a suitable dry time and the right amount of flexibility in the dried film are provided by a second main ingredient: acrylates copolymer, $C_{14}H_{22}O_6$, also known as ethyl prop-2-enoate; methyl 2-methylprop-2-enoate or 2-methylprop-2-enoic acid (IUPAC names); CAS number 25133-97-5. For detailed information, see PubChem Compound Database; CID=168299. In various types of cosmetic formulations, acrylates copolymer has a wide variety of uses including as film formers, hair fixatives, binders, and suspending agents, viscosity enhancers, antistatic agents and adhesives. At concentrations discussed herein, the combination of acrylates/VA copolymer and acrylates copolymer has a dry time that is suitable for the cosmetics consumer, which we define as two minutes or less, preferably one minute or less. Furthermore, as noted above, acrylates/VA copolymer films feature a temperature dependence, such that a water rinse of at least about 38° C. will degrade the film, but not below this. In combining acrylates/VA copolymer with acrylates copolymer at the ratios disclosed herein, it was noted that the minimum water temperature that is required to degrade the dried film of the spray-on compositions could be varied in a controlled manner.

In the present invention, useful concentrations of acrylates copolymer are from 0.05% to 2.5%, for example 0.1% to 2%, or, for example 0.5% to 1.5%, preferably about 1.0% based on total weight of the composition. Concentration of acrylates copolymer a little above 2.5% will make the spray-on film forming compositions too difficult to remove from the skin. Acrylates copolymer is commercially available, for example, as Daitosol 5000AD from Daito Kasei Kogyo Co. Daitosol 5000AD is a 50% aqueous mixture of acrylates copolymer. Therefore, in order to achieve the concentrations of acrylates copolymer noted above, the concentration of Daitosol 5000AD should be about 0.1% to 5%, for example 0.2% to 4%, or for example 1.0% to 3.0%, preferably about 2% by total weight of the composition. Daitosol 5000AD is reported to have a pH of 5.5-7.5, a viscosity of 50-100 mPa-s, a glass transition temperature ($T_g$) of about −14° C.

Normal, healthy skin temperature varies, but may be taken to be between 36.5° C. and 37.5° C. Based on this, we can say that the ratio of the weight of acrylates/VA copolymer to the weight of acrylates copolymer is in the range 1.8:1 to 280:1. Preferably this ratio is 10:1 to 100:1, more preferably 10:1 to 30:1, and most preferably 20:1. When the ratio is 1.8:1, then the spray-on film forming compositions of the invention (and adjacent cosmetic or skincare preparation) may be easily removed from the skin when lightly scrubbed with water a temperature of at least about 42° C. When the ratio is 280:1, then the spray-on film forming composition may be easily removed from the skin when lightly scrubbed with water a temperature of at least about 38° C. A ratio of 20:1 is most preferred. At 20:1, the spray-on film forming composition and adjacent cosmetic or skincare preparation are easily removed when lightly scrubbed with water at about 39° C.

Plasticizer

Compositions of the invention are aqueous, and typically comprise from about 70% to about 85% of water by weight of the total composition. This amount of water is that from all sources, such as that in Vinysol 2140L and Daitosol 5000AD. However, aqueous compositions of the invention, as so far described, are not sprayable from a mechanical pump sprayer of the type commonly used in the cosmetic industry. At best, a narrow stream of product is produced, with little or no atomization upon striking the atmosphere. This is unacceptable for a product that is intended to cover a relatively large area with a thin film. For this reason, a third main ingredient is one or more of butylene glycol, propanediol and glycerine. In the spray-on film forming compositions of the invention, these ingredients act as plasticizers, and have multiple beneficial effects on the film forming compositions. For example, these materials increase sprayability of the wet composition, as well as increase flexibility of the dried film, which increases comfort. The plasticizers do this by increasing the porosity of the film forming composition. When a preferred composition of the invention is applied to a substrate and allowed to dry, the dried film will have an average porosity between 0.25 μm to 3.0 μm, for example 0.9 μm to 2.5 μm. Butylene glycol, propanediol, glycerine, or any combination thereof, at 1% to 5% can be used to achieve that pore size.

Additionally, these same plasticizers play another beneficial role. The spray on film forming compositions of the present invention should have high adhesion for the adjacent cosmetic or skincare preparation. Sufficiently high adhesion can be ensured if the surface tension of the dried film is within 10 mN/m (milli-newtons per meter) of the surface tension of the cosmetic or skincare preparation. A typical water-in-silicone or water-in-oil foundation product has a surface tension between about 20 mN/m and 50 mN/m. Water, which is makes up 70% to 85% of the spray-on film forming composition of the invention, has a surface tension of about 72 mN/m. Therefore, the surface tension of a film forming composition of the present invention typically needs to be lowered to be within 10 mN/m of the surface tension of the adjacent topical preparation. In general, increasing the level of one or more of butylene glycol, propanediol and glycerine in a composition of the invention will lower the surface tension of the composition. Advantageously, the surface tension of the spray-on film forming composition can be adjusted, as needed, by the use of 1% to 5% butylene glycol, propanediol, glycerine or any combination thereof. Thus, the benefits of sprayability, flexibility, comfort and adhesion are achieved by adjusting the total concentration of any combination of these ingredients to be about 1% to 5% by weight of the total composition.

Furthermore, at 1% to 5%, butylene glycol, propanediol and/or glycerine can be used to make small adjustments to the minimum water temperature at which the spray-on film forming composition and adjacent cosmetic or skincare preparation are easily removed from the skin. Specifically, due to the plasticizing effect, the minimum water temperature is adjusted downward. If too much of these plasticizers is used, (i.e. more than 5%) the temperature will be adjusted too low, the long wear and non-transferability benefits of the invention will be compromised.

Surfactants and Emulsifiers

One or more surfactants or emulsifiers may also be used to adjust surface tension. As noted above, compositions of the invention typically comprise from about 70% to about 85% of water by weight of the total composition. Some preferred embodiments of the present invention are single aqueous phase compositions, and have little to no oil or silicone. In other preferred embodiments the compositions are lightly emulsified oil-in-water emulsions. The emulsion embodiments are useful when a composition comprises fragrance oils, or when the composition will be used to deliver at least one oil soluble actives (such as vitamin E acetate) to a keratinic surface. However, one or more surfactants or emulsifiers can also be used in the present invention to adjust the surface tension of the spray-on film forming compositions. In general, increasing the level of surfactant or emulsifier will lower the surface tension of the film forming compositions. Whether used to adjust surface tension or to emulsify oil soluble ingredients, the one or more surfactants or emulsifiers should have an HLB between 8 and 12, and comprise no more than 2% of the total composition, typically between 0.01% to 2% of the total composition.

Carrageenan and Hyaluronic Acid

When a composition of the invention, as so far described, is applied to the skin, and allowed to dry completely, the composition may feel tacky to the user. The tacky feel can be alleviated by the use of carrageenan and/or hyaluronic acid at concentrations of about 0.1% to about 1.0%, without interfering with the benefits of the composition as described herein. As an added benefit, carrageenan has a slight plasticizing effect on acrylates/VA copolymer, with the effect of reducing agglomeration and particle size. Thus, when used, carrageenan increases the sprayability of the wet film forming composition of the invention, as well as reduces the tacky feel of the dried composition. Preferred compositions of the invention comprise carrageenan and/or hyaluronic acid as described.

Hydrophobic Materials

Prior to applying to a keratinic surface, the film forming compositions of the present invention are in a first or hydrophilic state. The ability to formulate with water soluble ingredients in this first state is advantageous. To maintain sufficient hydrophilicity in the first state, the use of hydrophobic materials should be limited to less than about 5% based on total weight of the composition, for example 0.001% to 5%; preferably less than 2%, more preferably less than about 0.25%. Materials that are partly hydrophilic and partly hydrophobic could possibly exceed these limits, based on the performance of the final composition. In some embodiments of the invention, it is preferable if the composition comprises no hydrophobic ingredients, such as hydrophobic oils or waxes. Oils are organic substances that are liquid at ambient temperature, such as esters, triglycerides, hydrocarbons and silicones. A typical wax used in cosmetic compositions is carnauba wax. In some embodiments of the invention, it is most preferable if the compositions contain no hydrophobic oils or waxes.

Structuring Agents

Agents that significantly interfere with the structure of the dried film will alter the certain minimum temperature of water required for removal of the film from the skin. Therefore, it is preferred if film forming compositions of the invention comprise a total of no more than 0.5% of structuring agents, for example 0.0001% to 0.5% of structuring agents, such as Carbopol®, wax, clay (such as bentonite) or stearic acid. More preferably, compositions of the invention comprise a total of no more than 0.001% of structuring agents. Most preferably, compositions of the invention comprise no structuring agents. A useful exception to this rule is sodium stearate. Unlike many structuring agents, sodium stearate is partly hydrophilic, which makes it suitable for an aqueous system. Although sodium stearate is partly hydrophobic, its use has not appeared to compromise the objectives of the present invention. This makes it especially useful in embodiments of the present invention when a structuring agent may be needed. Sodium stearate may be used as a structuring agent from 0.0001% to 4% by weight of the total film forming composition, More than that amount will begin to disrupt the acrylic bond strength which translates to less water resistance.

Polyurethane

Polyurethane tends to make compositions very rigid, and will alter the certain minimum temperature of water required for removal of the film from the skin or hair. Therefore, film forming compositions of the invention comprise no more than 0.5%, for example 0.0001% to 0.5%, of polyurethane. More preferably, compositions of the invention comprise no polyurethane.

Various Ingredients

Various ingredients may be included in the spray-on film forming compositions to fine tune the consumer experience or enhance the performance of the composition and the adjacent cosmetic or skincare preparation. Alcohols, for example, may be useful to speed up drying after application to the skin. Amounts of alcohol up to 5% may be useful. The film forming compositions may also comprise preservatives and antioxidants, typically up to about 2% by weight of the composition. Thickeners, viscosity decreasing agents, and/or pH adjusters (such as caustic soda) may be used as needed to create a consumer acceptable product, typically at levels of less than 1% by weight of the composition. At these levels, the foregoing named ingredients do not seem to adversely affect the useful properties of the spray-on film forming composition.

Compositions of the invention may comprise pigments. Preferably, the compositions will comprise a total of no more than 1%, for example 0.001% to 1% of pigments. Also, when a composition of the invention is used as a primer (see below), then the composition will be covered by a color makeup preparation or skincare preparation. In this case, it is preferred if the compositions have no pigment.

Active Delivery

As noted above, after drying on a substrate, preferred compositions of the invention will be porous, with an average pore size of 0.25 μm to 3.0 μm, more preferably 0.9 μm to 2.5 μm. This pore size makes the spray-on compositions of the present invention useful as a delivery vehicle for active ingredients. The 0.9 μm to 2.5 μm range of pore size is particularly useful for controlled or sustained release of active ingredients.

Active ingredients may be incorporated into the aqueous phase or oil phase (if there is one). Examples of hydrophilic (water soluble) actives include: algae extract, *Alpinia speciosa* leaf extract, *Alteromonas* ferment extract, ascorbyl acid glucoside (AA2G), *Citrullus lanatus* (watermelon) fruit extract, *Crataegus monogyna* (hawthorn) flower extract, hyaluronic acid, hydrolyzed yeast protein, *Lactobacillus* ferment, *matricaria* (chamomile) extract, *Lens esculenta* (lentil) fruit extract, *Paeonia suffruticosa* (peony) root extract, panthenol, *Pyrus malus* (apple) fruit extract and *Saccharum officinarum* extract. Each individual hydrophilic active is typically incorporated at no more than 5.0%, for example 0.0001% to 5%, by weight of the composition. Examples of hydrophobic (oil soluble) actives include *Anthemis nobilis* oil, bht (butylated hydroxytoluene), caffeine, *Cocos nucifera* (coconut) oil, salicylic acid, tetrahexyldecyl ascorbate and tocopheryl acetate. Each individual hydrophobic active is typically incorporated at no more than 1%, for example 0.0001% to 1%, by weight of the composition.

As already noted, prior to applying to a keratinic surface, the film forming compositions of the present invention are in a first or hydrophilic state. Upon curing or drying, the composition enters a second or hydrophobic state. In this state, the applied composition resists breakdown from sebum and moisture in the skin or atmosphere. However, the dried composition of the present invention may easily be washed off with water at or above that certain minimum temperature and an application of shear. Both shear and a certain minimum water temperature are needed to remove the dried film composition from the skin. For example, when the dried composition is exposed to water at or above a certain minimum temperature, the composition experiences a breakdown in structure, but does not otherwise dissolve in the applied water. Likewise, when the dried composition is exposed to shear (in the form of a typical vigorous scrubbing action), without water or with water below a certain minimum temperature, the composition remains in place, having excellent adhesion to the skin. To effect the removal of the composition from the skin, both shear (in the form of a typical scrubbing action) and water above a certain minimum temperature must be applied to the composition in order to lift it off of the keratinic surface. There are multiple ways to exploit this feature, as now discussed.

Spray-on Film Forming Composition as a Primer

A method of applying a cosmetic or skincare care preparation to a keratinic surface will be described. For purposes of explanation, the preparation will be a color foundation, but all cosmetic and skincare compositions are within the scope of this method. A spray-on film forming composition according to the present invention may be used as a primer composition by applying the spray-on film forming composition directly to a portion of keratinic surface, such as the skin. Once applied, the primer composition is allowed to cure, which it does relatively quickly (less than about two minutes) to a clear, essentially invisible dried film. Once dried, the cosmetic preparation is applied over the dried film of the primer composition in a usual manner. The cosmetic preparation is preferably a color cosmetic that is intended to remain on the skin, hair, lips or nails for at least several hours, such as at least 4 hours or at least 8 hours. Suitable color cosmetics may be in form of liquid, cream, gel, powder, stick or other. In particular, liquid foundations and waterproof cosmetics will benefit significantly when used in conjunction with a film forming composition of the present invention. For example, once the applied primer is dry, a liquid foundation may be applied over the primer composition in a usual manner. Due to the closeness in surface tension, the liquid foundation will be held in place by the primer composition, transforming the liquid foundation into a long wear product. If the surface tension of the primer composition is not sufficiently close to that of the liquid foundation, then the foundation will be susceptible to spreading out and smudging.

Furthermore, even if the cosmetic preparation is already designed for long wear, the primer composition allows it to be removed from the skin much more easily. For example, when it is desired to remove the cosmetic product from the skin, rinse the area with water above about 38° C. and lightly scrub. The primer lifts from the skin, taking the overlaying cosmetic preparation with it. The skin cleans thoroughly and easily. The same cosmetic preparation applied directly to the skin, and allowed to dry, will usually require significantly more time and effort to remove from the skin. In fact, completely removing all residue from the pores of the skin may be impossible.

Cosmetic preparations applied directly to skin tend to absorb sebum and perspiration, which degrades their performance and customer satisfaction. One important benefit of the present invention when used as a primer is that it reduces the amount of sebum and perspiration absorbed by the cosmetic preparation. The sebum and moisture do not easily penetrate the dried film in a typical amount of time that a cosmetic will be worn.

Spray-on Film Forming Composition as a Mask

Alternatively, a cosmetic or skincare preparation may be applied first, directly to the skin, and then a spray-on film forming composition of the invention may be used as an overcoat or mask that is applied over a cosmetic or skincare preparation. As an overcoat, the mask prevents transfer and smudging of the cosmetic or skincare preparation. If the cosmetic preparation is a color cosmetic, such as foundation, then it is preferable if the mask comprises no pigments or colorants. The mask, being very clear, will allow the color cosmetic to show through without distorting the color. At the same time, the mask provides a high shine or glossy appearance. This is beneficial because it allows the underlying cosmetic preparation to be formulated with a lower concentration of ingredients that are traditionally sued to create shine. Also, the mask may comprise active ingredients that are intended to benefit the skin.

On the other hand, If the cosmetic preparation is a skincare treatment, with actives for delivery into the skin, then the mask may comprise colorants. Also, the mask may comprise active ingredients that benefit the skin. These may be the same as those in the skincare preparation or different. When it is desired to remove the cosmetic or skincare preparation from the skin, rinse the area with water above about 38° C. and lightly scrub. As the primer rinses away, the adhesion to the underlying cosmetic preparation is sufficient to lift the preparation off of the skin, and out of the pores. The skin cleans thoroughly and easily.

In some preferred embodiments, compositions of the invention may be used as both a primer and a mask, combining the benefits of both uses. For example, a first layer of a spray-on film forming composition according to the present invention may be applied directly to the skin, and allowed to cure to a dried film, as described above. Once dried, a cosmetic preparation, such as a liquid foundation, or a skincare preparation such as a serum with active ingredients, is applied over the primer composition in a usual manner. Due to the closeness in surface tension, the liquid foundation will be held in place by the primer composition, transforming the liquid foundation into a long wear product. Next, a second layer of the spray-on film forming composition of the invention is applied over the cosmetic or skincare preparation, and allowed to cure to a dried film that overcoats the cosmetic or skincare preparation. This mask layer prevents transfer and smudging, while imparting a shine to the appearance of the skin. When it is desired to remove the cosmetic or skincare preparation from the skin, rinse the area with water above about 38° C. and lightly scrub. The primer layer lifts from the skin, taking the overlaying cosmetic or skin care preparation and mask layer with it. The skin cleans thoroughly and easily.

The following non-limiting examples illustrate the invention.

Example 1

| Phase | Ingredient | Concentration |
|---|---|---|
| 1 | water | 52.73 |
| 1 | sodium hyaluronate | 0.10 |
| 1 | carrageenan (3.55)/water (95.5%)/phenoxyethanol (1.0%) | 10.00 |
| 1 | sodium dehydroacetate | 0.30 |
| 1 | sodium benzoate | 0.05 |
| In main beaker, mix sequence 1 to solubilize until clear | | |
| 2 | ¹Daitosol 5000AD | 1.00 |
| 2 | ²Vinysol 2140L | 20.00 |
| add sequence 2 ingredients to main beaker | | |
| 3 | propanediol | 4.00 |
| In a separate beaker, heat sequence 3 | | |
| 4 | ³preservative system | 1.40 |
| 4 | ethylhexylglycerin (99.5%)/tocopherol (0.5%) | 0.30 |
| 4 | chamomile romaine oil | 0.02 |
| add sequence 4 to sequence 3, and mix to solubilize; then add to main beaker | | |
| 5 | Carbopol® 981 (2%)/phenoxyethanol (98%) | 10.00 |
| 6 | sodium hydroxide (30%)/water (70%) | 0.10 |

¹46.6% aqueous mixture of acrylates/VA copolymer
²50% aqueous mixture of acrylates copolymer
³0.1% phenoxyethanol/0.8% phenoxyethanol/chloroxylenol/0.5% hydroxyacetophenone

Example 2

| Phase | Ingredient | Concentration |
|---|---|---|
| 1 | water | 62.36 |
| 1 | caffeine | 0.20 |
| 1 | salicylic acid | 0.20 |
| 1 | sodium hyaluronate | 0.30 |
| 1 | sodium benzoate | 0.05 |
| In a main beaker mix sequence 1 until solubilized. | | |
| 2 | glycerine | 0.50 |
| 2 | propanediol | 3.00 |
| 2 | hydroxyacetophenone | 0.50 |
| 2 | phenoxyethanol (50%)/capryl glycol (10%) / ethylhexyl glycerin (20%) / hexylene glycol (5%) | 0.90 |
| premix sequence 2 until solubilized; add to main beaker | | |
| 3 | ¹Lysofix™ liquid | 0.50 |
| 3 | tocopherol acetate | 0.50 |
| 3 | BHT | 0.10 |
| 3 | tetrahexyldecyl ascorbate | 0.20 |
| 3 | cocos nucifera (coconut) oil | 0.10 |
| premix sequence 3; add to main beaker | | |
| 4 | water soluble actives provided in water and/or butylene glycol solvent | 5.00 |
| 4 | lactobacillus ferment | 0.04 |
| premix sequence 4; add to main beaker | | |
| 5 | panthenol | 0.50 |
| 5 | water | 2.00 |
| premix sequence 5; add to main beaker | | |
| 6 | ²Daitosol 5000AD | 1.00 |
| 6 | ³Vinysol 2140L | 20.00 |
| add sequence 6 ingredients to main beaker | | |
| 7 | sodium hydroxide | 0.05 |
| 7 | water | 2.00 |
| premix sequence 7 until solubilized; add to main beaker | | |

¹Lysofix TM liquid is 73% glycerine, 27% soybean seed extract
²46.6% aqueous mixture of acrylates/VA copolymer
³50% aqueous mixture of acrylates copolymer

What is claimed is:

1. A sprayable film forming composition comprising, by total weight of the composition:
   4.7% to 14% of acrylates/VA copolymer;
   0.05% to 2.5% of acrylates copolymer;
   70% to 85% of water;
   0.1% to 1.0% of carrageenan and/or hyaluronic acid;
   wherein: the ratio of acrylates/VA copolymer to acrylates copolymer is between 10:1 and 100:1, and
   wherein, when the film forming composition is applied to a substrate and allowed to dry, the dried film will have an average porosity between 0.25 μm to 3.0 μm.

2. The sprayable film forming composition of claim 1 wherein the ratio of acrylates/VA copolymer to acrylates copolymer is in the range 10:1 and 30:1, and the composition further comprises (by total weight of the composition):
   1% to 5% butylene glycol, propanediol, glycerine, or any combination thereof;
   no more than 5.0% of hydrophobic oils;
   no more than 2% of surfactants and emulsifiers;
   no more than 0.5% of polyurethane.

3. The sprayable film forming composition of claim 2 in the form of an oil-in-water emulsion, comprising 0.01% to 2% of emulsifier and at least one oil-soluble active in an oil phase.

4. The sprayable film forming composition of claim 2 having no hydrophobic oils.

5. The sprayable film forming composition of claim 2 having no surfactants or emulsifiers.

6. The sprayable film forming composition of claim 2 having no polyurethane.

7. The sprayable film forming composition of claim 1 wherein, when the film forming composition is applied to a substrate and allowed to dry, the dried film will have an average porosity between 0.9 μm to 2.5 μm.

8. The sprayable film forming composition of claim 1 further comprising at least one water soluble active.

9. The sprayable film forming composition of claim 8 wherein the at least one water soluble active is hyaluronic acid.

10. The sprayable film forming composition of claim 3 wherein the at least one oil soluble active is tocopheryl acetate.

11. A method of applying a cosmetic or skincare care preparation to a keratinic surface comprising the steps of:
   applying a first layer of the spray-on film forming composition according to claim 1 directly to a portion of the keratinic surface;
   allowing the first layer of spray-on film forming composition to cure to a dried film;
   applying the cosmetic or skincare care preparation over the dried film.

12. The method of claim 11 further comprising the steps of:
   applying a second layer of the spray-on film forming composition over the cosmetic or skincare preparation, and
   allowing the second layer of spray-on film forming composition to cure to a dried film.

13. A method of applying a cosmetic or skincare care preparation to a keratinic surface comprising the steps of:
   applying a cosmetic or skincare preparation directly to a portion of the keratinic surface;
   applying a spray-on film forming composition of claim 1 over the cosmetic or skincare preparation;
   allowing the spray-on film forming composition to cure to a dried film.

* * * * *